United States Patent [19]

Messina et al.

[11] 4,374,280
[45] Feb. 15, 1983

[54] PROCESS FOR THE PREPARATION OF DICUMYL PEROXIDE

[75] Inventors: Giuseppe Messina, Alghero; Mario D. Moretti, Sassari; Loreno Lorenzoni, Porto Torres, all of Italy

[73] Assignee: Euteco Impianti S.p.A., Milan, Italy

[21] Appl. No.: 324,144

[22] Filed: Nov. 23, 1981

[30] Foreign Application Priority Data

Feb. 12, 1980 [IT] Italy ............................... 26345 A/80

[51] Int. Cl.$^3$ ........................................... C07C 179/06
[52] U.S. Cl. ..................................................... 568/558
[58] Field of Search ................................. 568/558, 578

[56] References Cited

U.S. PATENT DOCUMENTS

| | | | |
|---|---|---|---|
| 2,691,683 | 10/1954 | Lorand et al. | 568/578 |
| 2,994,719 | 8/1961 | Farkas et al. | 568/578 |
| 3,829,503 | 8/1974 | Kato et al. | 568/558 |
| 3,954,880 | 5/1976 | Nakayama et al. | 568/578 |
| 4,266,081 | 5/1981 | Mizuno et al. | 568/578 |

FOREIGN PATENT DOCUMENTS

| | | | |
|---|---|---|---|
| 628315 | 5/1963 | Belgium | 568/558 |
| 2062054 | 6/1971 | Fed. Rep. of Germany | 568/578 |
| 2842044 | 4/1979 | Fed. Rep. of Germany | 568/578 |
| 792558 | 7/1958 | United Kingdom | 568/578 |
| 1243313 | 8/1971 | United Kingdom | 568/578 |

OTHER PUBLICATIONS

Davies et al, "J. Chemical Society", pp. 4669–4670, (1966).
Hawkins, "Organic Peroxides", (1961), pp. 26, 79, 98–99 and 220–222, E&F Spon Ltd., London.
Mitsui Pet., "Derwent Pat. Abs.", 1597064, vol. 3, No. 32, 6/8/64–12/8/64.

*Primary Examiner*—Werren B. Lone
*Attorney, Agent, or Firm*—Brumbaugh, Graves, Donohue & Raymond

[57] ABSTRACT

A process for the preparation of dicumyl peroxide by reaction of dimethylbenzyl hydroperoxide (cumene hydroperoxide) with dimethyl phenyl carbinol in the presence of a catalytic quantity of a phosphorous halide or oxyhalide is described. This catalyst gives good yields of the useful reaction product and a high selectivity.

7 Claims, No Drawings

PROCESS FOR THE PREPARATION OF DICUMYL PEROXIDE

The present invention relates to an improved process for the preparation of dicumyl peroxide by reaction of cumene hydroperoxide with dimethyl phenyl carbinol, in the presence of a catalytic quantity of a phosphorus halide or oxyhalide.

Dialkylperoxides in general and dicumyl peroxide in particular are widely used in the art as vulcanizing agents for resins and elastomers, as cross-linking agents for polyolefins and above all as radical polymerisation initiators for the formation of polymers and copolymers from vinyl and diene monomers. They are for example used in the preparation of polyvinyl chloride, polyethylene, polystyrene, polyacrylonitrile, polyvinyl acetate, styrene-butadiene copolymers, alkylstyrene resins, silicone rubbers and others.

A process used in the art for preparing dialkyl peroxides consists of bringing a hydroperoxide into contact with an olefin under reaction conditions. More particularly, in the case of dicumyl peroxide, cumene hydroperoxide is reacted with alpha-methyl styrene under the influence of an acid catalyst, as described, for example, in German patent Applications Nos. 2,035,127 and 2,016,108 and in the Japanese Patent Application No. 7952,005.

The disadvantages of the processes which make use of alpha-methyl styrene in the preparation of dicumyl peroxide lie essentially in the tendency of the alpha-methyl styrene to form dimers, resulting in lowering of the yields and selectivity of the reaction. The by-products which form are also difficult to separate from the useful reaction products.

Hence the process more usually adopted in the art consists of bringing cumene hydroperoxide into contact with dimethyl phenyl carbinol and reacting these compounds under the influence of a catalytic quantity of a Lewis or Bronsted acid.

In particular, the catalysts used for this purpose in the art are: acid earths (Y. Tsunoda et al, Kogyo Kagaku Zasshi, 63, 387–389 (1960)); silica-alumina (Japanese Pat. No. 15,970/64); oxalic acid (Belgian Pat. No. 628,315); zinc chloride (German Patent Application No. 2,842,044); and perchloric acid (V. L. Antonoskii et al. Khim Perekisnykl Soedin.Akad. Nauk. USSR, Inst..Obshch. i Neorgan.Khim., 1963, 240–248 and German Patent Application No. 2,062,054).

A basic disadvantage of the processes of the known art lies in the tendency of the cumene hydroperoxide to be hydrolysed by the acid catalyst, resulting in the consequent formation of by-products and a reduction in the yield of the useful reaction product.

Furthermore, in the case of catalysts which are insoluble in the reaction medium and which are thus used in the form of dispersions in the said medium, these often show a weak catalytic activity towards the reaction which bring the formation of the dicumyl peroxide.

Consequently relatively large quantities of catalyst are needed, resulting in increased costs and greater difficulties in separating and recovering the dicumyl peroxide from the final reaction products. On the other hand catalysts which are soluble in the reaction medium sometimes display an excessively high activity both in hydrolysing the cumene hydroperoxide, with the consequences mentioned above, and towards the reaction which brings about the formation of the dicumyl peroxide, with consequent difficulties in the proper control of the reaction.

It must also be noted that water is formed as a by-product of the reaction between cumene hydroperoxide and dimethyl phenyl carbinol. The catalytic activity of some catalysts is reduced by the presence of the water either as a result of dilution or as a result of interaction with the water formed.

The object of the present invention is to provide a process for the production of dicumyl peroxide which is free, or substantially free, from the disadvantages of the processes of the known art. More particularly, it is found that these disadvantages may be overcome, or at least largely reduced, by reacting the cumene hydroperoxide with dimethyl phenyl carbinol in the presence of catalytic quantities of a phosphorous halide or oxyhalide. It is in fact found that these catalysts are highly selective towards the reaction which brings about the formation of the dicumyl peroxide, while showing very little or no activity towards hydrolysis of the cumene hydroperoxide. Furthermore, phosphorous halides and oxyhalides disperse well in the reaction medium and the water which forms as the by-product of the reaction does not have any deleterious effect on their catalytic activity.

Accordingly, in the present invention the cumene hydroperoxide is brought into contact with a molar excess of dimethyl phenyl carbinol and, furthermore, the reaction is carried out in the presence of a catalytic quantity of phosphorous halides or oxyhalides until the conversion of the cumene hydroperoxide is complete, or substantially complete, and finally the dicumyl peroxide is recovered from the reaction mixture.

The reaction which brings about the formation of the dicumyl peroxide is as follows:

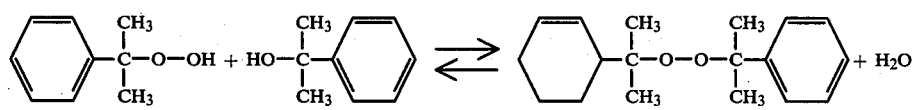

As is noted from the equation given above, water is formed as the by-product of the reaction and it is convenient to remove this water, which forms as the reaction proceeds, so as to displace the equilibrium towards the formation of dicumyl peroxide.

This reaction is catalysed by phosphorous halides and oxyhalides, and especially the chlorides, oxychlorides, bromides, oxybromides, fluorides and oxyfluorides of phosphorous. Of these $POCl_3$, $POBr_3$, $PBr_5$ and $POF_3$ are particularly useful, the first being preferred to the others. It should be noted that the phosphorous oxyhalides may be formed from the corresponding pentahalides by reaction with water and from the trihalides by oxidation by oxygen or peroxides.

The quantity of catalyst used generally varies from 0.5 to 2% by weight of the weight of the cumene hydroperoxide.

According to the present invention an excess of dimethyl phenyl carbinol with respect to the cumene hydroperoxide is used, the molar ratio between the dimethyl phenyl carbinol and the cumene hydroperoxide generally being within a range of values of from 1.2/1 to 5/1. The dimethyl phenyl carbinol which does not react with the cumene hydroperoxide is recovered at the end of the reaction in the form of alpha-methyl styrene.

The reaction which brings about the formation of the dicumyl peroxide occurs, in general, at a temperature of from ambient (20° to 25° C.) to 100° C., preferred values being in the range 30° to 60° C.

In order to remove the water from the reaction medium, the reaction is carried out at below atmospheric pressure and generally at a pressure of the order of 100 to 300 mmHg and/or with a flow of an inert gas such as nitrogen.

At the end of the reaction, the reaction mixture is neutralised by treatment with an aqueous base or by passage over basic exchange resins. The dicumyl peroxide is then separated from the neutralised mixture by cold crystallisation, or by steam distillation.

The process of the invention has a great many advantages.

Firstly the catalysts are for the most part liquid under ordinary conditions and are easy to disperse in the reaction medium. They are relatively cheap compared with the various catalysts of the known art.

The neutralisation and the washing of the reaction mixture do not give rise to any problems of an ecological nature since dilute aqueous solutions of alkali metal chlorides and phosphates are formed. Moreover, the use of the smaller quantity of catalyst, as indicated above, makes the treatment of the reaction mixture easier and more economical.

In every case the basic advantage of the use of the catalysts of the present invention lies in their high selectivity towards the useful reaction product (generally from 90 to 100% with respect to the cumene hydroperoxide) and in their slight or complete lack of tendency to hydrolyse the cumene hydroperoxide.

This selectivity of the catalyst is shown even with reagents which are not in the pure state. It is, in fact, an advantage of the process of the present invention that they allow the use of technical cumene hydroperoxide containing a quantity of cumene hydroperoxide higher than 85% by weight. Such cumene hydroperoxide, which can be obtained from the process for the production of phenol from cumene, contains acetophenone, cumene and butyl benzene as the main impurities, as well as a small quantity of dimethyl phenyl carbinol, which latter enters into the reaction with the cumene hydroperoxide.

EXAMPLE 1

There are loaded into a 100 ml glass flask 27.2 grams of dimethyl phenyl carbinol (0.2 moles), 0.1 ml of phosphorous oxychloride ($POCl_3$) and 9 grams of technical cumene hydroperoxide containing 88% by weight of cumene hydroperoxide (0.05 moles), the remaining percentage being made up essentially of dimethyl phenyl carbinol (7%), acetophenone (1.2%), cumene (3.5%) and butyl benzene (0.3%). All the percentages are given by weight.

The mixture is heated to 45° C. and is agitated and maintained at a pressure of 200 mmHg.

After two hours the molar conversion of the cumene hydroperoxide is 96.2% with a yield of 96.7 molar percent of dicumyl peroxide. The yield of the dicumyl peroxide with respect to the dimethyl phenyl carbinol is 56 molar percent. The remaining percentage of the dimethyl phenyl carbinol is recovered at the end of the reaction in the form of alpha-methyl styrene.

In addition to the dicumyl peroxide and alpha-methyl styrene, the reaction mixture contains small quantities of cumene and acetophenone introduced in the technical cumene hydroperoxide and small quantities of phenol and acetone resulting from hydrolysis of the cumene hydroperoxide.

The dicumyl peroxide is separated from the reaction mixture by cold crystallisation after neutralisation with an aqueous base.

EXAMPLE 2

There are loaded into a 100 ml glass flask 27.2 grams of dimethyl phenyl carbinol (0.2 moles), 0.1 ml of phosphorous oxychloride ($POCl_3$) and 9 grams of technical cumene hydroperoxide containing 88% by weight of cumene hydroperoxide (0.05 moles), identical to that of Example 1.

The mixture is heated to 60° C., agitated and maintained at a pressure of 200 mmHg.

After 30 minutes the cumene hydroperoxide is completely converted with a yield of 91 molar percent of dicumyl peroxide. The conversion of the dimethyl phenyl carbinol is 54 molar percent, with a yield of dicumyl peroxide of 42 molar percent. The remaining percentage is recovered at the end of the reaction in dehydrated form, that is in the form of alpha-methyl styrene.

In addition to the dicumyl peroxide and the alpha-methyl styrene, the reaction mixture contains the acetophenone and the cumene from the technical cumene hydroperoxide introduced initially, as well as small quantities of phenol and acetone resulting from hydrolysis of the cumene hydroperoxide.

The separation of the useful reaction product is carried out as explained in Example 1.

We claim:

1. A process for the preparation of dicumyl peroxide which comprises
   (a) reacting cumene hydroperoxide with a molar excess of dimethyl phenyl carbinol in the presence of from 0.5% to 2% by wt. with respect to the weight of cumene hydroperoxide of a catalyst consisting of phosphorous halides or oxyhalides,
   (b) maintaining the temperature in the reaction medium from about 20° to about 100° C., and
   (c) removing the water which forms from the reaction mixture while the reaction proceeds.

2. A process according to claim 1 wherein the said catalyst is selected from the group which comprises the chlorides, oxychlorides, bromides, oxybromides, fluorides and oxyfluorides of phosphorous.

3. A process according to claim 2 wherein the said catalyst is $POCl_3$ or $POBr_3$ or $PBr_5$ or $POF_3$.

4. A process according to claim 1 wherein the said molar excess of the dimethyl phenyl carbinol is from 1.2/1 to 5/1 with respect to cumene hydroperoxide.

5. A process according to claim 1 wherein the said water is removed at a reduced pressure of from about 100 mm Hg (136 millibar) to about 300 mm Hg (408 millibar).

6. A process according to claim 1 which comprises neutralising the reaction mixture after the cumene hydroperoxide is substantially reacted and then recovering the dicumyl peroxide by cold crystallization or by steam distillation.

7. A process according to claim 1 to 6 wherein the said cumene hydroperoxide is of technical grade with a cumene hydroperoxide content higher than about 85% by weight.

* * * * *

UNITED STATES PATENT AND TRADEMARK OFFICE
CERTIFICATE OF CORRECTION

PATENT NO. : 4,374,280
DATED : February 15, 1983
INVENTOR(S) : Giuseppe Messina et al.

It is certified that error appears in the above-identified patent and that said Letters Patent is hereby corrected as shown below:

First page, Item 30, "Feb. 12, 1980" should read -- Dec. 2, 1980 --.

Column 1, line 65, "bring" should read -- brings about --.

Signed and Sealed this

Fifteenth Day of May 1984

[SEAL]

Attest:

GERALD J. MOSSINGHOFF

Attesting Officer

Commissioner of Patents and Trademarks